(12) United States Patent
Schimperna et al.

(10) Patent No.: US 12,060,348 B2
(45) Date of Patent: Aug. 13, 2024

(54) PROCESS FOR THE PREPARATION OF DISUBSTITUTED DIARYLOXYBENZOHETERODIAZOLE COMPOUNDS

(71) Applicant: ENI S.P.A., Rome (IT)

(72) Inventors: Giuliana Schimperna, Novara (IT); Luca Beverina, Milan (IT); Mauro Sassi, Vedano Olona (IT)

(73) Assignee: ENI S.P.A., Rome (IT)

( * ) Notice: Subject to any disclaimer, the term of this patent is extended or adjusted under 35 U.S.C. 154(b) by 533 days.

(21) Appl. No.: 16/961,487

(22) PCT Filed: Jan. 9, 2019

(86) PCT No.: PCT/IB2019/050151
§ 371 (c)(1),
(2) Date: Jul. 10, 2020

(87) PCT Pub. No.: WO2019/138332
PCT Pub. Date: Jul. 18, 2019

(65) Prior Publication Data
US 2020/0339560 A1    Oct. 29, 2020

(30) Foreign Application Priority Data
Jan. 10, 2018 (IT) .................. 102018000000667

(51) Int. Cl.
*C07D 417/14* (2006.01)
(52) U.S. Cl.
CPC .................. *C07D 417/14* (2013.01)
(58) Field of Classification Search
None
See application file for complete search history.

(56) References Cited

FOREIGN PATENT DOCUMENTS

| | | |
|---|---|---|
| CN | 107001353 A | 1/2017 |
| WO | 2012007834 A1 | 1/2012 |
| WO | 20160046310 A1 | 3/2016 |
| WO | 20160046319 A1 | 3/2016 |
| WO | 20170081645 A1 | 5/2017 |

OTHER PUBLICATIONS

India Office Action dated Feb. 9, 2022 for India Patent Appl. No. 202017029500.
International Search Report dated Feb. 25, 2019 for PCT application No. PCT/IB2019/050151.
Written Opinion dated Feb. 25, 2019 for PCT application No. PCT/IB2019/050151.
Chinese First Office Action dated Mar. 15, 2023 from corresponding Chinese Patent Application No. 201980007845.4, 23 pages.
Mattiello, Sara et al.; "Suzuki Miyaura Micellar Cross-Coupling in Water, at Room Temperature, and under Aerobic Atmosphere", Org. Lett., vol. 19, pp. 654-657.

*Primary Examiner* — Po-Chih Chen
(74) *Attorney, Agent, or Firm* — Ruggiero McAllister & McMahon LLC

(57) ABSTRACT

Process for the preparation of a disubstituted diaryloxybenzoheterodiazole compound having general formula (I):

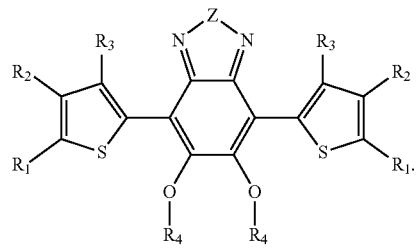

(I)

13 Claims, No Drawings

PROCESS FOR THE PREPARATION OF DISUBSTITUTED DIARYLOXYBENZOHETERODIAZOLE COMPOUNDS

The present invention relates to a process for preparing a disubstituted diaryloxybenzoheterodiazole compound.

More in particular, the present invention relates to a process for preparing a diaryloxybenzoheterodiazole compound disubstituted with thiophene groups comprising various steps, wherein some of said steps are carried out in the presence of air and of a mixture comprising water and at least one non-ionic surfactant ("micellar synthesis").

The disubstituted diaryloxybenzoheterodiazole compound thus obtained can be advantageously used as a spectrum converter in luminescent solar concentrators (LSCs) in turn able to improve the performance of photovoltaic devices (or solar devices) selected, for example, from photovoltaic cells (or solar cells), photovoltaic modules (or solar modules), both on rigid supports or flexible supports.

Diaryloxybenzoheterodiazole compounds disubstituted with thiophene groups can be synthesized through processes with various steps, known in the state of the art as described, for example, in international patent application WO 2016/046319. However, said processes, although efficient in terms of absolute yields, make wide use of organic solvents which are also toxic such as, for example, 1,4-dioxane. Moreover, in said processes, aryl-alkyl stannanes can be used which, as well as being toxic reactants as such, lead to the formation of alkyl stannanes, the disposal of which, in compliance with legislation in force on the management of pollutants, is very expensive. Furthermore, some of the steps of said processes are carried out at a temperature ranging from 80° C. to 110° C., for a time ranging from 12 to 18 hours, and the different intermediates obtained in the various steps, generally need to be purified through elution on a silica gel chromatography column and/or recrystallization by organic solvents, prior to use thereof in the subsequent steps.

It is therefore of interest to find processes that do not use toxic compounds, which reduce the process times and temperatures, with consequent savings both in terms of energy consumption, and in terms of process costs.

In fact, over recent years, with the changing mentality that sees the environment as something to be protected and safeguarded, increased interest in so-called "green chemistry" has also grown in the chemical world. Many studies have been done to make many organic chemical reactions environmentally friendly. A great effort has been made to prevent or reduce the amount of toxic solvents used, to reduce the process times and temperatures, with consequent savings both in terms of energy consumption, and in terms of process costs.

For the aforesaid purpose, in the past, ionic liquids have been studied which have been used as solvents in many organic chemical reactions: however, because of their cost, said ionic liquids did not turn out to be of particular interest especially in view of the industrial use thereof. Supercritical carbon dioxide or fluorinated solvents have also been studied as solvents to be used in organic chemical reactions.

It is however easy to deduce that the least polluting solvent possible is water, which is therefore the ideal solvent of choice to be used in organic chemical reactions. However, it is not always possible to use water because many organic substances are not water soluble unless small quantities of surfactants are added to the water. Surfactants are organized in water by forming micelles into which the organic molecules present in the reaction can enter: said micelles act as small reactors in which various chemical reactions can take place i.e. so-called "micellar synthesis".

Many studies have been done in relation to said "micellar synthesis" as described, for example, in the review by La Sorella G. et al, in "*Green Chemistry*" (2015), Vol. 17, Issue 2, pag. 644-683.

The abovementioned "micellar synthesis" can also be used for catalyzed metal reactions such as, for example, Stille, Suzuki and Sonogashira reactions.

For example, studies have been carried out to improve the catalysts containing palladium used in Suzuki reactions through said "micellar synthesis" as described, for example, in the article by Lipshutz B. H. et al, in "Science" (2015), Vol. 349, Issue 6252, pag. 1087-1091. Said article reports the use of nanoparticles formed by iron(III) chloride containing small percentages of palladium as catalysts in Suzuki-Miyaura reactions. Said reactions are carried out in the presence of a surfactant and the nanomicelles formed are used both for solubilizing the reactants and for the subsequent reaction with the catalysts.

Lipshutz B. H. et al, in an article in "*Angewandte Communications*" (2014), Vol. 53, pag. 3432-3435, report the synthesis of β-ketosulfones starting from aryl alkynes (for example, phenylacetylene) and sulfinic acid (for example, sodium salt of β-toluenesulfinic acid), at room temperature, in the presence of an aqueous solution containing 2% by weight of TPGS-750-M as surfactant and of 2,6-lutidine.

However, there are organic chemical reactions in which the presence of oxygen is detrimental, such as in the case of a Suzuki-Miyaura reaction. Therefore, in this case, it is necessary for the chemical reaction to take place in an inert environment, in a nitrogen or argon atmosphere. For the purpose of overcoming this drawback, it is possible to create micelles in water that do not contain oxygen as described, for example, in the article by Beverina L. et al, in "*Organic Letters*" (2017), Vol. 19(3), pag. 654-657. Said article reports the Suzuki-Miyaura cross-coupling reaction in water, at room temperature, in the presence of oxygen, thanks to the use of aqueous solutions of the surfactant Kolliphor® EL which are able to form nanomicelles with oxygen-free cores.

The Applicant therefore set out to solve the problem of finding a process for the preparation of disubstituted diaryloxybenzoheterodiazole compounds which is more environmentally friendly, both able to reduce the amount of organic solvents used, and to reduce the process times and temperatures, with consequent savings both in terms of energy consumptions and in terms of process costs.

The Applicant has now found a process for the preparation of disubstituted diaryloxybenzoheterodiazole compounds that can be carried out by exploiting the aforesaid "micellar synthesis". In particular, the Applicant has found a process for the preparation of disubstituted diaryloxybenzoheterodiazole compounds comprising various steps, wherein some of said steps are carried out in the presence of air and of a mixture comprising water and at least one non-ionic surfactant ("micellar synthesis").

Numerous advantages are obtained through the abovementioned process such as, for example:
  in said process, the intermediates obtained at the end of each step do not require further purification through elution on a silica gel chromatography column prior to being used in the subsequent steps;
  in said process, boronic compounds are used and the use of toxic stannilated compounds is completely avoided;
  in said process, the steps carried out by exploiting the abovementioned "micellar synthesis", allow a reduction in the quantity of organic solvents used with respect to processes of the prior art;

in said process, the steps carried out by exploiting the abovementioned "micellar synthesis", allow both a reduction in reaction times, i.e. they are carried out with reaction times less than or equal to 70 minutes, and a reduction in reaction temperatures, i.e. they are carried out at temperatures less than or equal to 90° C., with respect to processes of the prior art;

in said process, the steps carried out by exploiting the abovementioned "micellar synthesis", are carried out in the presence of air and of water as the main solvent hence avoiding having to operate in an inert atmosphere despite the presence of catalysts containing palladium which can be oxidized in the presence of air.

Therefore the subject matter of the present invention is a process for the preparation of a disubstituted diaryloxybenzoheterodiazole compound having general formula (I):

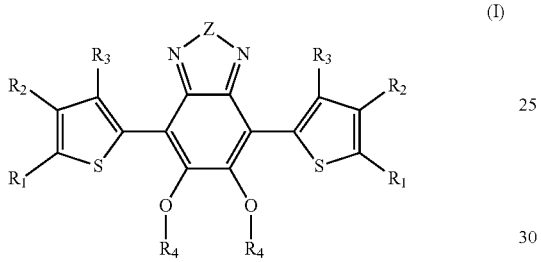

(I)

wherein:

Z represents a sulfur atom, an oxygen atom, a selenium atom; or an $NR_5$ group wherein $R_5$ is selected from linear or branched $C_1$-$C_{20}$, preferably $C_1$-$C_8$, alkyl groups, or from optionally substituted aryl groups;

$R_1$, $R_2$ and $R_3$, identical or different, represent a hydrogen atom; or they are selected from linear or branched, $C_1$-$C_{20}$, preferably $C_1$-$C_8$, alkyl groups, optionally containing heteroatoms, optionally substituted cycloalkyl groups, optionally substituted aryl groups, linear or branched, optionally substituted, $C_1$-$C_{20}$, preferably $C_1$-$C_8$, alkoxy groups, optionally substituted phenoxy groups, —$COOR_6$ groups wherein $R_6$ is selected from linear or branched, $C_1$-$C_{20}$, preferably $C_1$-$C_8$, alkyl groups, or is a cyano group;

or $R_1$ and $R_2$, can be optionally linked together so as to form, together with the carbon atoms to which they are linked, a saturated, unsaturated, or aromatic cycle or polycyclic system containing from 3 to 14 carbon atoms, preferably from 4 to 6 carbon atoms, optionally containing one or more heteroatoms such as, for example, oxygen, sulfur, nitrogen, silicon, phosphorus, selenium;

or $R_2$ and $R_3$, can be optionally linked together so as to form, together with the carbon atoms to which they are linked, a saturated, unsaturated, or aromatic cycle or polycyclic system containing from 3 to 14 carbon atoms, preferably from 4 to 6 carbon atoms, optionally containing one or more heteroatoms such as, for example, oxygen, sulfur, nitrogen, silicon, phosphorus, selenium;

$R_4$, identical or different, are selected from optionally substituted aryl groups; comprising the following steps:

(a) reacting at least one halogenated benzoheterodiazole compound having general formula (II):

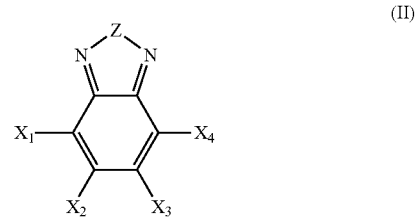

(II)

wherein Z has the same meanings described above, $X_1$ and $X_4$, identical or different, preferably identical, and $X_2$ and $X_3$, identical or different, preferably identical, represent a halogen atom such as, for example, chlorine, bromine, fluorine, iodine, preferably bromine, fluorine, even more preferably $X_1$ and $X_4$, represent a bromine atom and $X_2$ and $X_3$ represent a fluorine atom or a chlorine atom, provided that $X_1$ and $X_4$ are different from $X_2$ and $X_3$, with at least one 2-thienyl boronic compound having general formula (III):

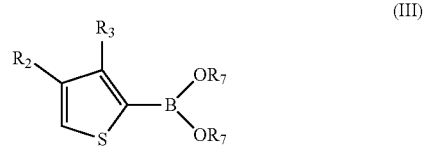

(III)

wherein $R_2$ and $R_3$ have the same meanings described above and the $R_7$ substituents, identical or different, represent a hydrogen atom, or they are selected from linear or branched $C_1$-$C_{10}$ alkyl groups, or from optionally substituted cycloalkyl groups, or the two $R_7$ substituents can be optionally linked together so as to form, together with the other atoms to which they are linked, a cycle as in the case of pinacol esters of boronic acid or 1,3-propanediol esters of boronic acid, preferably represent a hydrogen atom, obtaining a halogenated disubstituted benzoheterodiazole compound having general formula (IV):

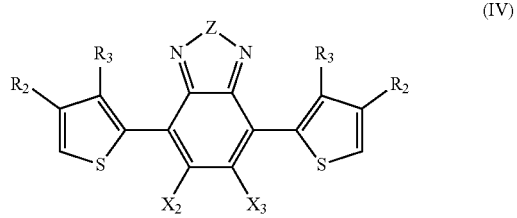

(IV)

wherein Z, $R_2$, $R_3$, $X_2$ and $X_3$, have the same meanings described above;

(b) reacting the halogenated disubstituted benzoheterodiazole compound having general formula (IV) obtained in step (a) with at least one aryl alcohol having general formula (V):

$R_4$—OH (V)

wherein R₄ has the same meanings described above, obtaining a disubstituted diaryloxybenzoheterodiazole compound having general formula (VI):

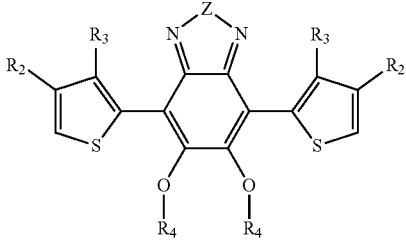

(VI)

wherein Z, R₂, R₃ and R₄, have the same meanings described above; and, in the case wherein the R₁ substituents in the disubstituted diaryloxybenzoheterodiazole compound having general formula (I) are different from hydrogen,
(c) reacting the disubstituted diaryloxybenzoheterodiazole compound having general formula (VI) obtained in step (b) with at least one N-haloimide such as N-bromosuccinimide, N-bromophthalimide, N-chlorosuccinimide, N-chlorophthalimide, N-iodosuccinimide, N-iodophthalimide, preferably N-bromosuccinimide, obtaining a halogenated disubstituted diaryloxybenzoheterodiazole compound having general formula (VII):

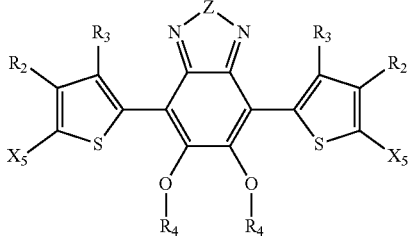

(VII)

wherein Z, R₂, R₃ and R₄ have the same meanings described above, and X₅ represents a halogen atom such as, for example, chlorine, bromine, iodine, preferably bromine;
(d) reacting the halogenated disubstituted diaryloxybenzoheterodiazole compound having general formula (VII) obtained in step (c) with at least one boronic compound having general formula (VIII):

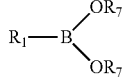

(VIII)

wherein R₁ and R₇, have the same meanings described above, provided that R₁ is different from hydrogen;
wherein:
said step (a) is carried out in the presence of air and of a mixture comprising water, at least one non-ionic surfactant and, optionally, at least one hydrocarbon solvent;
said step (d) is carried out in the presence of air and of a mixture comprising water, at least one non-ionic surfactant, at least one hydrocarbon solvent.

For the purpose of the present description and of the following claims, the definitions of the numeric ranges always include the extremes unless specified otherwise.

For the purpose of the present description and of the following claims, the term "comprising" also includes the terms "which essentially consists of" or "which consists of".

For the purpose of the present description and of the following claims, the term "in the presence of air" means that it is not necessary to operate in an inert atmosphere.

For the purpose of the present description and of the following claims, the term "$C_1$-$C_{20}$ alkyl groups" means alkyl groups having from 1 to 20 carbon atoms, linear or branched.

Specific examples of $C_1$-$C_{20}$ alkyl groups are: methyl, ethyl, n-propyl, iso-propyl, n-butyl, iso-butyl, t-butyl, pentyl, 2-ethyl-hexyl, hexyl, heptyl, octyl, nonyl, decyl, dodecyl.

For the purpose of the present description and of the following claims, the term "$C_1$-$C_{20}$ alkyl groups optionally containing heteroatoms" means alkyl groups having from 1 to 20 carbon atoms, linear or branched, saturated or unsaturated, wherein at least one of the hydrogen atoms is substituted with a heteroatom selected from: halogen atoms such as, for example, fluorine, chlorine, preferably fluorine; nitrogen; sulfur; oxygen. Specific examples of $C_1$-$C_{20}$ alkyl groups optionally containing heteroatoms are: fluoromethyl, difluoromethyl, trifluoromethyl, trichloromethyl, 2,2,2-trifluoroethyl, 2,2,2-trichloroethyl, 2,2,3,3-tetrafluoropropyl, 2,2,3,3,3-pentafluoropropyl, perfluoropentyl, perfluorooctyl, perfluorodecyl, oxymethyl, thiomethyl, thioethyl, dimethylamine, propylamine, dioctylamine.

For the purpose of the present description and of the following claims, the term "cycloalkyl groups" means cycloalkyl groups having from 3 to 10 carbon atoms. Said cycloalkyl groups can be optionally substituted with one or more groups, identical or different, selected from: halogen atoms such as, for example, fluorine, chlorine, preferably fluorine; hydroxyl groups; $C_1$-$C_{20}$ alkyl groups, $C_1$-$C_{20}$ alkoxy groups; cyano groups; amino groups; nitro groups; aryl groups. Specific examples of cycloalkyl groups are: cyclopropyl, 1,4-dioxine, 2,2-difluorocyclopropyl, cyclobutyl, cyclopentyl, cyclohexyl, methylcyclohexyl, methoxycyclohexyl, fluorocyclohexyl, phenylcyclohexyl.

For the purpose of the present description and of the following claims, the term "aryl groups" means carbocyclic aromatic groups. Said aryl groups can be optionally substituted with one or more groups, identical or different, selected from: halogen atoms such as, for example, fluorine, chlorine, preferably fluorine; hydroxyl groups; $C_1$-$C_2$ alkyl groups; $C_1$-$C_{20}$ alkoxy groups; cyano groups; amino groups; nitro groups; aryl groups.

Specific examples of aryl groups are: phenyl, diphenyl, methylphenyl, dimethylphenyl, trimethylphenyl, di-iso-propylphenyl, t-butylphenyl, methoxyphenyl, hydroxyphenyl, phenyloxyphenyl, fluorophenyl, pentafluorophenyl, chlorophenyl, nitrophenyl, dimethylaminophenyl, naphthyl, phenylnaphthyl, phenanthrene, anthracene.

For the purpose of the present description and of the following claims, the term "$C_1$-$C_{20}$ alkoxy groups" means alkoxy groups having from 1 to 20 carbon atoms, linear or branched. Said alkoxy groups can be optionally substituted with one or more groups, identical or different, selected from: halogen atoms such as, for example, fluorine, chlorine, preferably fluorine; hydroxyl groups; $C_1$-$C_{20}$ alkyl groups, $C_1$-$C_{20}$ alkoxy groups; cyano groups; amino groups; nitro groups. Specific examples of $C_1$-$C_{20}$ alkoxy groups are: methoxy, ethoxy, fluoroethoxy, n-propoxy, iso-propoxy, n-butoxy, n-fluoro-butoxy, iso-butoxy, t-butoxy, pentoxy, hexyloxy, heptyloxy, octyloxy, nonyloxy, decyloxy, dodecyloxy.

For the purpose of the present description and of the following claims, the term "optionally substituted phenoxy groups" means $C_6H_5O$ phenoxy groups optionally substituted with one or more groups, identical or different, selected from: halogen atoms such as, for example, fluorine, chlorine, preferably fluorine; $C_1$-$C_{20}$ alkyl groups; $C_1$-$C_{20}$ alkoxy groups; cyano groups; amino groups; nitro groups. Specific examples of $C_6H_5O$ phenoxy groups are: phenoxy, 4-nitrophenoxy, 2,4-di-nitrophenoxy, 2-chloro-4-nitrophenoxy, 2-fluoro-4-nitrophenoxy, 3-fluoro-4-nitrophenoxy, 5-fluoro-2-nitrophenoxy, 2-aminophenoxy.

In accordance with a preferred embodiment of the present invention, in said general formula (I):

Z represents a sulfur atom;

$R_1$, identical, represent a hydrogen atom; or they are selected from optionally substituted aryl groups, preferably they are 2,6-dimethylphenyl, 2,5-dimethylphenyl, 3,5-dimethylphenyl;

$R_2$ and $R_3$, identical, represent a hydrogen atom;

$R_4$, identical, are selected from optionally substituted aryl groups, preferably they are phenyl, t-butylphenyl, naphthyl, 2,6-dimethylphenyl, diphenyl.

Specific examples of compounds having general formula (I) that can be obtained through the process according to the present invention are provided in Table 1.

TABLE 1

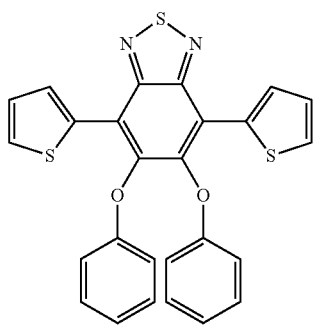 [SMILES: c1ccc(Oc2c(Oc3ccccc3)c(-c3cccs3)c3nsnc3c2-c2cccs2)cc1]

(Ia)

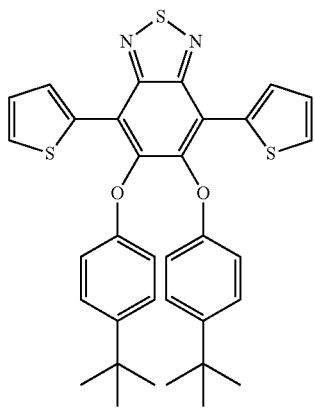 [SMILES: CC(C)(C)c1ccc(Oc2c(Oc3ccc(C(C)(C)C)cc3)c(-c3cccs3)c3nsnc3c2-c2cccs2)cc1]

(Ib)

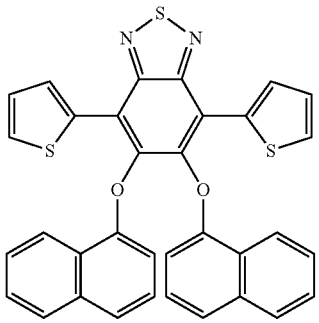 [SMILES: c1csc(-c2c(Oc3cccc4ccccc34)c(Oc3cccc4ccccc34)c(-c3cccs3)c3nsnc23)c1]

(Ic)

TABLE 1-continued
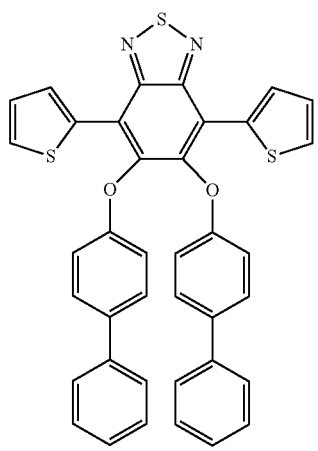
(Id)
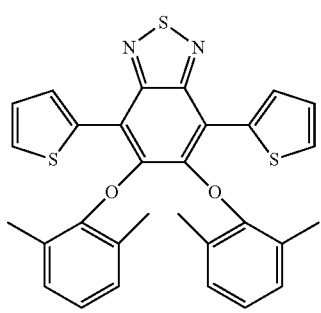
(Ie)
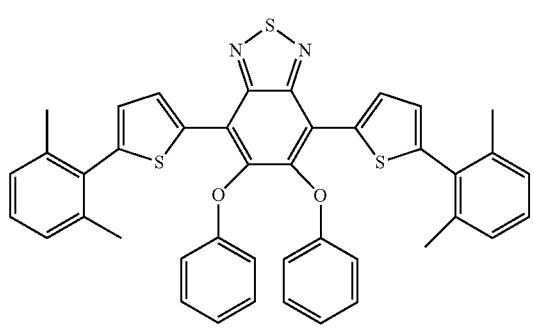
(If)
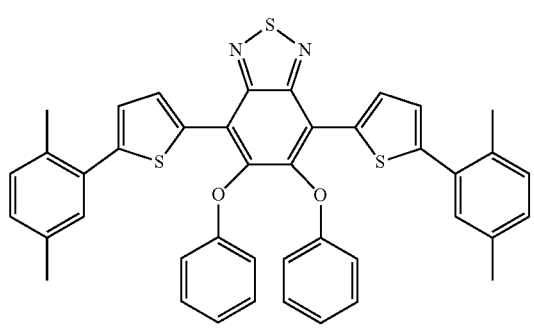
(Ig)

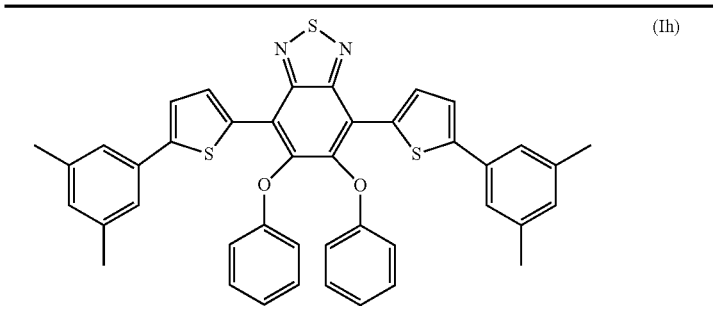
(Ih)

In accordance with a preferred embodiment of the present invention, in said step (a), said halogenated benzoheterodiazole compound having general formula (II) and said 2-thienylboronic compound having general formula (III) can be used in molar ratios ranging from 1:2 to 1:4, preferably ranging from 1:2.2 to 1:3.2.

In accordance with a preferred embodiment of the present invention, said step (a) can be carried out in the presence of at least one catalyst comprising palladium that can be selected, for example, from palladium compounds in an oxidation state of (0) or (II) such as, for example, [1,1'-bis(di-tert-butylphosphino)ferrocene]dichloropalladium(II) [Pd(dtbpf)Cl$_2$], tetrakis(triphenylphosphine)palladium [Pd(PPh$_3$)$_4$], bis(triphenylphosphine)palladium(II) dichloride [PdCl$_2$(PPh$_3$)$_2$], preferably [1,1'-bis(di-tert-butylphosphino)ferrocene]dichloropalladium(I1) [Pd(dtbpf)Cl$_2$]. Preferably, said halogenated benzoheterodiazole compound having general formula (II) and said catalyst can be used in molar ratios ranging from 100:1 to 100:3, preferably ranging from 100:1.5 to 100:2.5.

In accordance with a preferred embodiment of the present invention, said step (a) can be carried out in the presence of at least one organic base that can be selected, for example, from aliphatic or cycloaliphatic tertiary amines such as, for example, trimethylamine, triethylamine, tri-iso-propylamine, diethyl-iso-propylamine, di-iso-propylethylamine, 1,4-diazabicyclo[2.2.2]octane (DABCO), or mixtures thereof; preferably triethylamine. Preferably, said halogenated benzoheterodiazole compound having general formula (II) and said organic base can be used in molar ratios ranging from 1:2 to 1:7, preferably ranging from 1:1 to 1:6.5.

In accordance with a preferred embodiment of the present invention, in said step (a), said non-ionic surfactant can be selected, for example, from non-ionic surfactants having an HLB ("hydrophilic-lipophilic balance") greater than or equal to 10, preferably ranging from 11 to 16.

In accordance with a preferred embodiment of the present invention, in said step (a), said non-ionic surfactant can be selected, for example, from amphiphilic surfactants containing a polar group and a polyoxyethylene group such as, for example, polyoxyethylated castor oil (Kolliphor® EL by Aldrich), mixture of polyglycol mono- and di-esters of hydroxystearic acid and free polyethylene glycol (Kolliphor® HS-15 by Aldrich), tert-octylphenoxypolyethoxyethanol (Triton™ by Aldrich), DL-α-tocopherol methoxypolyethylene glycol succinate (TPGS-750-M by Aldrich); preferably polyoxyethylated castor oil (Kolliphor® EL by Aldrich).

In accordance with a preferred embodiment of the present invention, in said step (a), said hydrocarbon solvent, optionally present, can be selected, for example, from: aromatic hydrocarbons such as, for example, toluene, xylene, isopropylbenzene, or mixtures thereof; aliphatic hydrocarbons such as, for example, heptane, octane, decane, or mixtures thereof; or mixtures thereof; preferably toluene.

In accordance with a preferred embodiment of the present invention, in said step (a) said mixture comprising water, at least one non-ionic surfactant and, optionally, at least one hydrocarbon solvent, comprises:
- an aqueous solution comprising from 0.1% by weight to 20% by weight, preferably from 0.5% by weight to 10% by weight, with respect to the total weight of said aqueous solution, of said at least one non-ionic surfactant; and, optionally,
- at least one hydrocarbon solvent, the volumetric ratio between said aqueous solution of said at least one non-ionic surfactant and said hydrocarbon solvent being ranging from 8:2 to 10:0, preferably ranging from 9:1 to 10:0.

In accordance with a preferred embodiment of the present invention, said benzoheterodiazole compound having general formula (II) can be used in said mixture in a quantity such as to have a molar concentration in said mixture ranging from 0.1 M to 1 M, preferably ranging from 0.2 M to 0.6 M.

In accordance with a preferred embodiment of the present invention, said step (a) can be carried out at a temperature ranging from 25° C. to 80° C., preferably ranging from 30° C. to 75° C.

In accordance with a preferred embodiment of the present invention, said step (a) can be carried out for a time ranging from 20 minutes to 60 minutes, preferably ranging from 25 minutes to 40 minutes.

Generally, at the end of said step (a) the mixture obtained, after removal of the solvent and of the organic base through evaporation at reduced pressure, is diluted with water and subjected to filtration obtaining a precipitate that is taken up with alcohol (e.g., methanol) subjected again to filtration and used as such in the subsequent step (b).

In accordance with a preferred embodiment of the present invention, in said step (b), said halogenated disubstituted benzoheterodiazole compound having general formula (IV) and said aryl alcohol having general formula (V) can be used in molar ratios ranging from 1:2 to 1:10, preferably ranging from 1:2 to 1:5.

In accordance with a preferred embodiment of the present invention, said step (b) can be carried out in the presence of at least one weak organic base that can be selected, for example, from: carboxylates of alkali metal (e.g., sodium, potassium, cesium) or of alkaline-earth metal (e.g., magnesium, calcium) such as, for example, potassium acetate, sodium acetate, cesium acetate, magnesium acetate, calcium acetate, potassium propionate, sodium propionate, cesium propionate, magnesium propionate, calcium propionate, or mixtures thereof; carbonates of alkali metal (e.g., lithium, sodium, potassium, cesium) or of alkaline-earth metal (e.g., magnesium, calcium) such as, for example, lithium carbonate, potassium carbonate, sodium carbonate, cesium carbonate, magnesium carbonate, calcium carbonate, or mixtures thereof; preferably potassium carbonate, sodium carbonate, cesium carbonate. Preferably, said halogenated disubstituted benzoheterodiazole compound having general formula (IV) and said weak organic base can be used in molar ratios ranging from 1:1 to 1:10, preferably ranging from 1:2 to 1:5.

In accordance with a preferred embodiment of the present invention, said step (b) can be carried out in the presence of at least one organic solvent that can be selected, for example, from hydrocarbons such as, for example toluene, xylene, or mixtures thereof; dipolar aprotic solvents such as, for example N,N-dimethylformamide, N-methylpyrrolidone, dimethyl sulfoxide, or mixtures thereof; or mixtures thereof; preferably N,N—N-dimethylformamide.

In accordance with a preferred embodiment of the present invention, in said step (b) said disubstituted halogenated benzoheterodiazole compound having general formula (IV) can be used in said organic solvent in a quantity such as to have a molar concentration in said organic solvent ranging from 0.05 M to 2 M, preferably ranging from 0.1 M to 1 M.

In accordance with a preferred embodiment of the present invention, said step (b) can be carried out in the presence of at least one crown ether, which can be selected, for example, from: 18-crown-6, dibenzo-18-crown-6, dicyclohexyl-18-crown-6, dibenzo-24-crown-8, 12-crown-4, 15-crown-5, cyclohexyl-12-crown-4, tribenzo-18-crown-6, tetrabenzo-18-crown-6, dibenzo-26-crown-6, or mixtures thereof; preferably 18-crown-6.

Preferably, said crown ether can be used in a quantity ranging from 1 mol % to 10 mol %, preferably ranging from 2 mol % to 8 mol %, with respect to the moles of said weak organic base.

In accordance with a preferred embodiment of the present invention, said step (b) can be carried out at a temperature ranging from 60° C. to 95° C., preferably ranging from 75° C. to 90° C.

In accordance with a preferred embodiment of the present invention, said step (b) can be carried out for a time ranging from 1 hour to 24 hours, preferably ranging from 2 hours to 12 hours.

Generally, at the end of said step (b) the mixture obtained is diluted with water and subjected to filtration obtaining a precipitate that is taken up with alcohol (e.g., methanol) subjected again to filtration and used as such in step (b).

In accordance with a preferred embodiment of the present invention, in said step (c), said disubstituted diaryloxybenzoheterodiazole compound having general formula (VI) and said N-haloimide can be used in molar ratios ranging from 1:2 to 1:3, preferably ranging from 1:2 to 1:2.5.

In accordance with a preferred embodiment of the present invention, said step (c) can be carried out in the presence of at least one organic solvent that can be selected, for example, from: ethers such as, for example, 1,2-dimethoxyethane, 1,4-dioxane, tetrahydrofuran, 2-methyl-tetrahydrofuran, or mixtures thereof; preferably tetrahydrofuran.

In accordance with a preferred embodiment of the present invention, said disubstituted diaryloxybenzoheterodiazole compound having general formula (IV) can be used in said organic solvent in a quantity such as to have a molar concentration in said organic solvent ranging from 0.01 M to 5 M, preferably ranging from 0.1 M to 2 M.

In accordance with a preferred embodiment of the present invention, said step (c) can be carried out at a temperature ranging from 20° C. to 50° C., preferably ranging from 23° C. to 30° C.

In accordance with a preferred embodiment of the present invention, said step (c) can be carried out for a time ranging from 1 hour to 24 hours, preferably ranging from 4 hours to 18 hours.

Generally, at the end of said step (c) the suspension obtained is dried by evaporation at reduced pressure, obtaining a precipitate that is taken up with alcohol (e.g., methanol) subjected to filtration and used as such in step (d).

In accordance with a preferred embodiment of the present invention, in said step (d), said halogenated disubstituted diaryloxybenzoheterodiazole compound having general formula (VII) and said boronic compound having general formula (VIII) can be used in molar ratios ranging from 1:2 to 1:4, preferably ranging from 1:2.2 to 1:3.2.

In accordance with a preferred embodiment of the present invention, said step (d) can be carried out in the presence of at least one catalyst comprising palladium that can be selected, for example, from palladium compounds in an oxidation state of (0) or (II) such as, for example, [1,1'-bis(di-tert-butylphosphino)ferrocene]dichloropalladium(II) [Pd(dtbpf)Cl$_2$], tetrakis(triphenylphosphine)palladium [Pd(PPh$_3$)$_4$], bis(triphenylphosphine)palladium(II) dichloride [PdCl$_2$(PPh$_3$)$_2$], preferably [1,1'-bis(di-tert-butylphosphino)ferrocene]dichloropalladium(II) [Pd(dtbpf)Cl$_2$]. Preferably, said disubstituted halogenated diaryloxybenzoheterodiazole compound having general formula (VII) and said catalyst can be used in molar ratios ranging from 100:1 to 100:3, preferably ranging from 100:1.5 to 100:2.5.

In accordance with a preferred embodiment of the present invention, said step (d) can be carried out in the presence of at least one organic base that can be selected, for example from aliphatic or cycloaliphatic tertiary amines such as, for example, trimethylamine, triethylamine, tri-iso-propylamine, diethyl-iso-propylamine, di-iso-propylethylamine, 1,4-diazabicyclo[2.2.2]octane (DABCO), or mixtures thereof; preferably triethylamine.

Preferably, said halogenated disubstituted diaryloxybenzoheterodiazole compound having general formula (VII) and said organic base can be used in molar ratios ranging from 1:2 to 1:7, preferably ranging from 1:1 to 1:6.5.

In accordance with a preferred embodiment of the present invention, in said step (d), said non-ionic surfactant can be selected, for example, from non-ionic surfactants having an HLB ("hydrophilic-lipophilic balance") greater than or equal to 10, preferably ranging from 11 to 16.

In accordance with a preferred embodiment of the present invention, in said step (d), said non-ionic surfactant can be selected, for example, from amphiphilic surfactants containing a polar group and a polyoxyethylene group such as polyoxyethylated castor oil (Kolliphor® EL by Aldrich), mixture of polyglycol mono- and di-esters of hydroxystearic acid and free polyethylene glycol (Kolliphor® HS-15 by Aldrich), tert-octylphenoxypolyethoxyethanol (Triton™ by Aldrich), DL-α-tocopherol methoxypolyethylene glycol succinate (TPGS-750-M by Aldrich); preferably polyoxyethylated castor oil (Kolliphor® EL by Aldrich).

In accordance with a preferred embodiment of the present invention, in said step (d), said hydrocarbon solvent can be selected, for example, from: aromatic hydrocarbons such as, for example, toluene, xylene, iso-propylbenzene, or mixtures thereof; aliphatic hydrocarbons such as, for example, heptane, octane, decane, or mixtures thereof; or mixtures thereof; preferably toluene.

In accordance with a preferred embodiment of the present invention, in said step (d) said mixture comprising water, at least one non-ionic surfactant and at least one hydrocarbon solvent, comprises:

- an aqueous solution comprising from 0.1% by weight to 20% by weight, preferably from 0.5% by weight to 10% by weight, with respect to the total weight of said aqueous solution, of said at least one non-ionic surfactant;
- at least one hydrocarbon solvent, the volumetric ratio between said aqueous solution of said at least one non-ionic surfactant and said hydrocarbon solvent being ranging from 7:3 to 8:2, preferably ranging from 8.5:2.5 to 9:1.

In accordance with a preferred embodiment of the present invention, said halogenated disubstituted diaryloxybenzoheterodiazole compound having general formula (VII) can be used in said mixture in a quantity such as to have a molar concentration in said mixture ranging from 0.1 M to 1 M, preferably ranging from 0.2 M to 0.6 M.

In accordance with a preferred embodiment of the present invention, said step (d) can be carried out at a temperature ranging from 25° C. to 90° C., preferably ranging from 30° C. to 85° C.

In accordance with a preferred embodiment of the present invention, said step (d) can be carried out for a time ranging from 20 minutes to 70 minutes, preferably ranging from 30 minutes to 65 minutes.

Generally, water is added to the mixture obtained at the end of said step (d) and the product is extracted with solvent (e.g., dichloromethane) obtaining an organic phase.

Subsequently, after washing said organic phase to neutrality with water, the solvent is removed by evaporation at reduced pressure and the product obtained is subjected to purification through normal purification methods such as elution on a silica gel chromatography column and/or crystallization by organic solvents such as, for example: hydrocarbons (e.g., n-heptane, hexane, toluene, or mixtures thereof); chlorinated solvents (e.g., dichloromethane, chloroform, or mixtures thereof); ester solvents (e.g., ethyl acetate, methyl acetate, methyl propinate, or mixtures thereof); ether solvents (e.g., ethyl ether, tetrahydrofuran, t-butylmethylether, or mixtures thereof); alcohols (e.g., methanol, ethanol, propanol, or mixtures thereof); or mixtures thereof.

The halogenated benzoheterodiazole compounds having general formula (II), the 2-thienylboronic compounds having general formula (III), the aryl alcohols having general formula (V), the N-haloimides and the boronic compounds having general formula (VIII), are commercially available.

As described above, said disubstituted diaryloxybenzoheterodiazole compound having general formula (I) can be advantageously used as a spectrum converter in luminescent solar concentrators (LSCs) in turn able to improve the performance of photovoltaic devices (or solar devices) such as, for example, photovoltaic cells (or solar cells), photovoltaic modules (or solar modules), both on rigid supports or flexible supports.

For the purpose of understanding the present invention better and to put it into practice, below are some illustrative and non-limiting examples thereof.

EXAMPLE 1

Synthesis of 5,6-diphenoxy-4,7-bis[2-thienyl]benzo[c]2,5-thiadiazole (DTBOP) having formula (Ia)

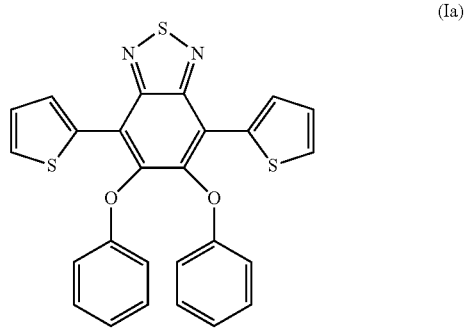 [SMILES: c1ccc(Oc2c(Oc3ccccc3)c(-c3cccs3)c3nsnc3c2-c2cccs2)cc1]

(Ia)

Step (a)

Synthesis of 5,6-difluoro-4,7-bis[2-thienyl]benzo[c]1,2,5-thiadiazole

In a 100 ml flask, with a mechanical stirrer, thermometer and coolant, in the presence of air, at room temperature (25° C.), under stirring, triethylamine (10.2 ml, 73.26 mmol) (Aldrich) was added to a suspension of 4,7-dibromo-5,6-difluorobenzothiadiazole (4.03 g, 12.21 mmol) (Santailab), 2-thienylboronic acid (4.70 g, 36.63 mmol) (Aldrich) and [1,1'-bis(di-tert-butylphosphino)ferrocene]dichloropalladium(II) [Pd(dtbpf)Cl$_2$] (Aldrich) (0.15 g, 0.24 mmol) (Aldrich), in 15 ml of a 9:1 (v/v) mixture of Kolliphor® EL (2% solution by weight in deionized water) (Aldrich) and toluene (Aldrich): the reaction mixture obtained was heated to 70° C. and maintained, under stirring, at said temperature, for 30 minutes (the colour of the reaction mixture rapidly turns yellow/very dark brown). Subsequently, the toluene and triethylamine were removed by evaporation at reduced pressure in a rotary evaporator and, after adding 100 ml of distilled water, a precipitate was obtained which was recovered through filtration, taken up with 50 ml of methanol (Aldrich) and then recovered again through filtration obtaining 4.04 g (12.0 mmol) of an orange/brown solid product corresponding to 5,6-difluoro-4,7-bis[2-thienyl]benzo[c]1,2,5-thiadiazole (yield=98%).

Step (b)

Synthesis of 5,6-diphenoxy-4,7-bis[2-thienyl]benzo[c]1,2,5-thiadiazole (DTBOP) having formula (Ia)

In a 100 ml flask, with a mechanical stirrer, thermometer and coolant, in an inert atmosphere, at room temperature (25° C.), under stirring, 5,6-difluoro-4,7-bis[2-thienyl]benzo[c]1,2,5-thiadiazole (6.50 g, 19.32 mmol) obtained as described in step (a), phenol (7.0 g, 74.38 mmol) (Aldrich), potassium carbonate (7.48 g, 54.0 mmol) (Aldrich) and 18-crown-6 (0.8 g, 3.03 mmol) (Aldrich), were suspended in 50 ml of N,N-dimethylformamide anhydrous (Aldrich): the suspension obtained was heated to 80° C. and maintained, under stirring, at said temperature, for 10 hours, obtaining a very dark viscous solution. Said solution was poured slowly into 200 ml of water, obtaining a yellow precipitate that was recovered through filtration, taken up with 200 ml of hot methanol (Aldrich) and then recovered again through filtration obtaining 9.0 g (18.6 mmol) of a yellow solid product corresponding to 5,6-diphenoxy-4,7-bis[2-thienyl]benzo[c] 1,2,5-thiadiazole (DTBOP) having formula (Ia) (yield=96%).

EXAMPLE 2

Synthesis of 5,6-diphenoxy-4,7-bis[5-(2,6-dimethylphenyl)-2-thienyl]benzo[c]2,5-thiadiazole (MPDTBOP) having formula (If)

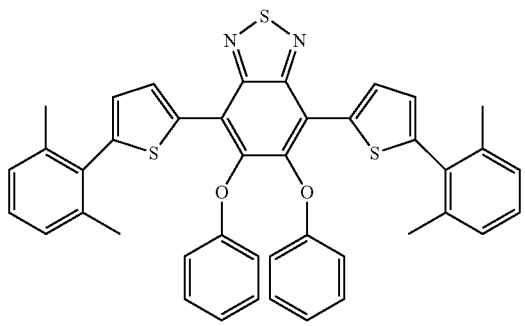

(If)

Step (c)

Synthesis of 5,6-diphenoxy-4,7-bis[5-bromo-2-thienyl]benzo[c]1,2,5-thiadiazole

In a 100 ml flask, with a magnetic stirrer, in an inert atmosphere, at room temperature (25° C.), under stirring, N-bromosuccinimide (6.3 g, 35.4 mmol) (Aldrich), freshly crystallized, was added in small portions in 10 minutes to a suspension of 5,6-diphenoxy-4,7-bis[2-thienyl]benzo[c]1,2,5-thiadiazole (DTBOP) having formula (Ia) (8.2 g, 16.92 mmol) obtained as described in Step (b) of Example 1, in 80 ml of tetrahydrofuran anhydrous (Aldrich): the orange suspension obtained was maintained, under stirring, for 1 night, at room temperature (25° C.), in the absence of light. Subsequently, the suspension obtained was dried by evaporation at reduced pressure in a rotary evaporator obtaining a precipitate that was taken up with 150 ml of methanol (Aldrich) obtaining a dark orange suspension. From said suspension, 10.2 g (15.9 mmol) of a bright orange solid product corresponding to 5,6-diphenoxy-4,7-bis[5-bromo-2-thienyl]benzo[c]1,2,5-thiadiazole (yield=94%) was recovered, through vacuum filtration.

Step (d)

Synthesis of 5,6-diphenoxy-4,7-bis[5-(2,6-dimethylphenyl)-2-thienyl]benzo[c]1,2,5-thiadiazole (MPDTBOP) having formula (if)

In a 100 ml flask, with a mechanical stirrer, thermometer and coolant, in the presence of air, at room temperature (25° C.), under stirring, triethylamine (21 ml, 150 mmol) (Aldrich) was added to a suspension of 5,6-diphenoxy-4,7-bis [5-bromo-2-thienyl]benzo[c]1,2,5-thiadiazole (16.0 g, 24.9 mmol) obtained as described in Step (c), 2,6-dimethyl-phenyl boronic acid (11.25 g, 75.0 mmol) (Aldrich) and [1,1'-bis(di-tert-butylphosphino)ferrocene]dichloropalladium(II) [Pd(dtbpf)Cl$_2$] (Aldrich) (0.78 g, 1.2 mmol) (Aldrich), in 30 ml of a 9:1 (v/v) mixture of Kolliphor® EL (2% solution by weight in deionized water) (Aldrich) and toluene (Aldrich): the reaction mixture obtained was heated to 80° C. and maintained, under stirring, at said temperature, for 1 hour (the colour turns dark red). The reaction mixture was then poured into water (400 ml) and extracted with dichloromethane (Aldrich) (3×25 ml). The organic phase obtained was washed to neutrality with water (3×25 ml), and then anhydrified on sodium sulfate (Aldrich). The residual solvent was removed by evaporation at reduced pressure in a rotary evaporator. The residual waxy red solid obtained was purified through elution on a silica gel chromatography column [eluent: mixture of n-heptane (Aldrich)/dichloromethane (Aldrich)/ethyl acetate (Aldrich) in a 85/10/5 (v/v)ratio], dried in the oven at 80° C., taken up with 150 ml of methanol (Aldrich) and recovered again through filtration obtaining 15.53 g (22.41 mmol) of a bright orange solid product 5,6-diphenoxy-4,7-bis[5-(2,6-dimethylphenyl)-2-thienyl]benzo[c]1,2,5-thiadiazole (MPDTBOP) having formula (If) (yield=90%).

EXAMPLE 3

Synthesis of 5,6-diphenoxy-4,7-bis[5-(2,5-dimethylphenyl)-2-thienyl]benzo[c]2,5-thiadiazole (PPDTBOP) having formula (Iq)

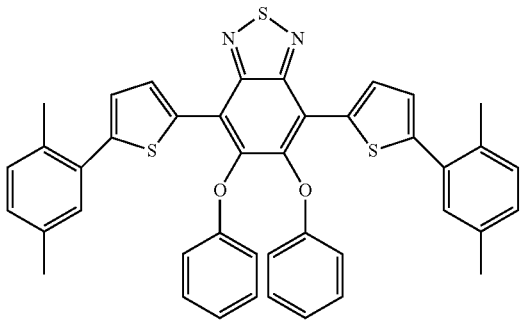

(Ig)

Step (d)

In a 100 ml flask, with a mechanical stirrer, thermometer and coolant, in the presence of air, at room temperature (25° C.), under stirring, triethylamine (21 ml, 150 mmol) (Aldrich) was added to a suspension of 5,6-diphenoxy-4,7-bis [5-bromo-2-thienyl]benzo[c]1,2,5-thiadiazole (16.0 g, 24.9 mmol) obtained as described in Step (c) of Example 2, 2,5-dimethyl-phenyl boronic acid (11.25 g, 75.0 mmol) (Aldrich) and [1,1'-bis(di-tert-butylphosphino)ferrocene]dichloropalladium(II) [Pd(dtbpf)Cl$_2$] (Aldrich) (0.78 g, 1.2 mmol) (Aldrich), in 30 ml of a 9:1 (v/v) mixture of Kolliphor® EL (2% solution by weight in deionized water) (Aldrich) and toluene (Aldrich): the reaction mixture obtained was heated to 80° C. and maintained, under stirring, at said temperature, for 1 hour (the colour turns dark red). The reaction mixture was then poured into water (400 ml) and extracted with dichloromethane (Aldrich) (3×25 ml). The organic phase obtained was washed to neutrality with water (3×25 ml), and then anhydrified on sodium sulfate (Aldrich). The residual solvent was removed by evaporation at reduced pressure in a rotary evaporator. The residual waxy red solid obtained was purified through elution on a silica gel chromatography column [eluent: mixture of n-heptane (Aldrich)/dichloromethane (Aldrich)/ethyl acetate (Aldrich) in a 85/10/5 (v/v) ratio], dried in the oven at 80° C., taken up with 150 ml of methanol (Aldrich) and recovered again through filtration obtaining 13.8 g (20 mmol) of a bright orange solid product 5,6-diphenoxy-4,7-bis[5-(2,5-dimethylphenyl)-2-thienyl]benzo[c]1,2,5-thiadiazole (PPDTBOP) having formula (Ig) (yield=80%).

The invention claimed is:

1. A process for the preparation of a disubstituted diaryloxybenzoheterodiazole compound having general formula (I):

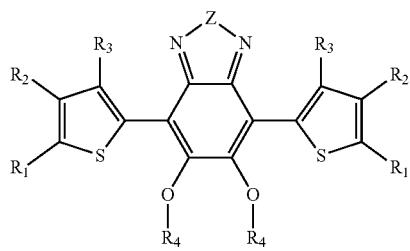

(I)

wherein:

Z represents a sulfur atom;

$R_1$, identical, represent a hydrogen atom or are selected from the group consisting of 2,6-dimethylpenyl, 2,5-dimethylphenyl, and 3,5 dimethylphenyl $R_2$ and $R_3$, identical, represent a hydrogen atom; and $R_4$, identical, are selected from the group consisting of phenyl, t-butylphenyl, naphthyl, and 2,6-dimethylphenyl;

comprising the following steps:

(a) reacting at least one halogenated benzoheterodiazole compound having general formula (II):

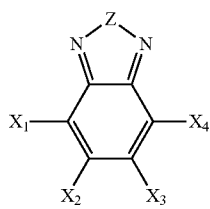

(II)

wherein Z has the same meaning as in formula (I), $X_1$ and $X_4$, identical or different, and $X_2$ and $X_3$, identical or different, represent a halogen atom selected from the group consisting of chlorine, bromine, fluorine, and iodine, or $X_1$ and $X_4$ optionally represent a bromine atom and $X_2$ and $X_3$ optionally represent a fluorine atom or a chlorine atom provided that $X_1$ and $X_4$ are different from $X_2$ and $X_3$ with at least one 2-thienylboronic compound having general formula (III):

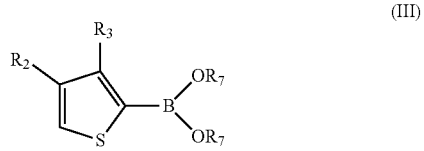

(III)

wherein $R_2$ and $R_3$ have the same meanings as in formula (I) and the $R_7$ substituents, identical or different, represent a hydrogen atom, or they are selected from linear or branched $C_1$-$C_{10}$ alkyl groups, or from optionally substituted cycloalkyl groups, or the two $R_7$ substituents can be optionally linked together so as to form, together with the other atoms to which they are linked, a cycle selected from pinacol esters of boronic acid or 1,3-propanediol esters of boronic acid obtaining a halogenated disubstituted benzoheterodiazole compound having general formula (IV):

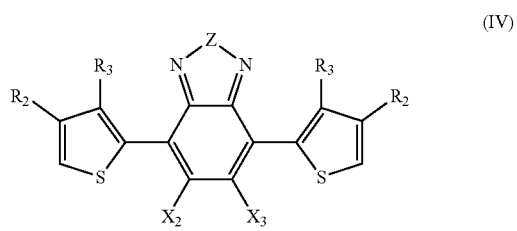

(IV)

wherein Z, $R_2$, $R_3$, $X_2$ and $X_3$ have the same meanings as in formula (I);

(b) reacting the halogenated disubstituted benzoheterodiazole compound having general formula (IV) obtained in step (a) with at least one aryl alcohol having general formula (V):

$R_4$—OH  (V)

wherein $R_4$ has the same meanings as in formula (I), obtaining a disubstituted diaryloxybenzoheterodiazole compound having general formula (VI):

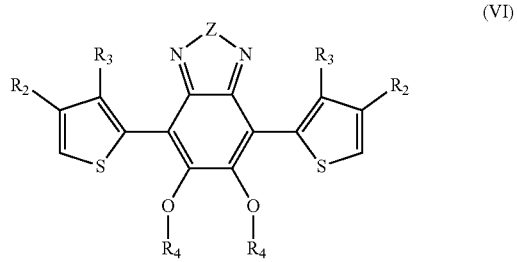

(VI)

wherein Z, $R_2$, $R_3$ and $R_4$ have the same meanings as in formula (I); and, in the case wherein the $R_1$ substituents in the disubstituted diaryloxybenzoheterodiazole compound having general formula (I) are different from hydrogen, (c) reacting the disubstituted diaryloxybenzoheterodiazole compound having general formula (VI) obtained in step (b) with at least one N-haloimide selected from the group consisting of N-bromosuccinimide, N-bromophthalimide, N-chlorosuccinimide, N-chlorophthalimide, and N-iodosuccinimide, N-iodophthalimide, obtaining a halogenated disubstituted diaryloxybenzoheterodiazole compound having general formula (VII):

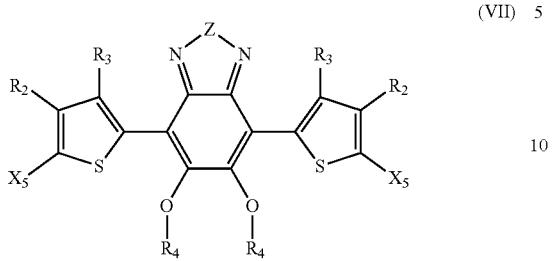

wherein Z, $R_2$, $R_3$ and $R_4$ have the same meanings as in formula (I), and $X_5$ represents a halogen atom selected from the group consisting of chlorine, bromine, fluorine, and iodine; and (d) reacting the halogenated disubstituted diaryloxybenzoheterodiazole compound having general formula (VII) obtained in step (c) with at least one boronic compound having general formula (VIII):

wherein $R_1$ has the same meanings as in formula (I) and $R_7$ has the same meaning as in formula (III), provided that $R_1$ is different from hydrogen;

wherein:
said step (a) is carried out in the presence of air and of a mixture comprising water, at least one non-ionic surfactant and, optionally, at least one hydrocarbon solvent;
said step (d) is carried out in the presence of air and of a mixture comprising water, at least one non-ionic surfactant, and at least one hydrocarbon solvent.

2. The process for the preparation of a disubstituted diaryloxybenzoheterodiazole compound having general formula (I) according to claim 1, wherein:

in said step (a), said halogenated benzoheterodiazole compound having general formula (II) and said 2-thienylboronic compound having general formula (III) are used in molar ratios ranging from 1:2 to 1:4, and/or said step (a) is carried out in the presence of at least one catalyst containing palladium selected from the group consisting of [1,1'-bis(di-tert-butylphosphino)ferrocene]dichloropalladium (II) [Pd(dtbpf)Cl$_2$], palladium-tetrakistriphenylphosphine [Pd(PPh$_3$)$_4$], and bis-triphenylphosphine palladium dichloride [PdCl$_2$(PPh$_3$)$_2$]; said halogenated benzoheterodiazole compound having general formula (II) and said catalyst being used in molar ratios ranging from 100:1 to 100:3; and/or said step (a) is carried out in the presence of at least one organic base selected from the group consisting of trimethylamine, triethylamine, tri-iso-propylamine, diethyl-iso-propylamine, di-isopropylethylamine, 1,4-diazabicyclo[2.2.2]octane (DABCO), and mixtures thereof; said halogenated benzoheterodiazole compound having general formula (II) and said organic base being used in molar ratios ranging from 1:2 to 1:7; and/or in said step (a), said non-ionic surfactant is selected from non-ionic surfactants having a hydrophilic-lipophilic balance (HLB) greater than or equal to 10; and/or in said step (a), said hydrocarbon solvent, optionally present, is selected from the group consisting of aromatic hydrocarbons; aliphatic hydrocarbons; or mixtures thereof; and/or in said step (a) said mixture comprising water, at least one non-ionic surfactant and, optionally, at least one hydrocarbon solvent, comprises:
an aqueous solution comprising from 0.1% by weight to 20% by weight with respect to the total weight of said aqueous solution, of said at least one non-ionic surfactant; and, optionally,
at least one hydrocarbon solvent, volumetric ratio between said aqueous solution of said at least one non-ionic surfactant and said hydrocarbon solvent being ranging from 8:2 to 10:0;

said halogenated benzoheterodiazole compound having general formula (II) being used in said mixture in an amount as to have a molar concentration in said mixture ranging from 0.1 M to 1 M; and/or said step (a) is carried out at a temperature ranging from 25° C. to 80° C.; and/or said step (a) is carried out for a time ranging from 20 minutes to 60 minutes.

3. The process for the preparation of a disubstituted diaryloxybenzoheterodiazole compound having general formula (I) according to claim 1, wherein:

in said step (b), said halogenated disubstituted benzoheterodiazole compound having general formula (IV) and said aryl alcohol having general formula (V) are used in molar ratios ranging from 1:2 to 1:10; and/or said step (b) is carried out in the presence of at least one weak organic base selected from alkali metal carboxylates selected from the group consisting of potassium acetate, sodium acetate, cesium acetate, magnesium acetate, calcium acetate, potassium propionate, sodium propionate, cesium propionate, magnesium propionate, calcium propionate, and mixture thereof; and alkali metal carbonates selected from the group consisting of lithium carbonate, potassium carbonate, sodium carbonate, cesium carbonate, magnesium carbonate, calcium carbonate, and mixtures thereof; said halogenated disubstituted benzoheterodiazole compound having general formula (IV) and said weak organic base being used in molar ratios ranging from 1:1 to 1:10; and/or said step (b) is carried out in the presence of at least one organic solvent selected from hydrocarbons selected from the group consisting of toluene, xylene, or mixtures thereof; and dipolar aprotic solvents selected from the group consisting of N,N-dimethylformamide, N-methylpyrrolidone, dimethyl sulfoxide, and mixtures thereof; said halogenated disubstituted benzoheterodiazole compound having general formula (IV) being used in said organic solvent in an amount as to have a molar concentration in said organic solvent ranging from 0.05 M to 2 M; and/or said step (b) is carried out in the presence of at least one crown ether selected from the group consisting of 18-crown-6, dibenzo-18-crown-6, dicyclohexyl-18-crown-6, dibenzo-24-crown-8, 12-crown-4, 15-crown-5, cyclohexyl-12-crown-4, tribenzo-18-crown-6, tetrabenzo-18-crown-6, dibenzo-26-crown-6, and mixtures thereof; said crown ether being used in an amount ranging from 1 mol % to 10 mol % with respect to the moles of said weak organic base; and/or said step (b) is carried out at a temperature ranging from 60° C. to 95° C.; and/or said step (b) is carried out for a time ranging from 1 hour to 24 hours.

4. The process for the preparation of a disubstituted diaryloxybenzoheterodiazole compound having general formula (I) according to claim 1, wherein:

in said step (c), said disubstituted diaryloxybenzoheterodiazole compound having general formula (VI) and said N-haloimide are used in molar ratios ranging from 1:2 to 1:3; and/or said step (c) is carried out in the presence of at least one organic solvent selected from the group consisting of 1,2-dimethoxyethane, 1,4-dioxane, tetrahydrofuran, 2-methyl-tetrahydrofuran, or mixtures thereof; said disubstituted diaryloxybenzoheterodiazole compound having general formula (VI) being used in said organic solvent in an amount as to have a molar concentration in said organic solvent ranging from 0.01 M to 5 M; and/or said step (c) is carried out at a temperature ranging from 20° C. to 50° C.; and/or said step (c) is carried out for a time ranging from 1 hour to 24 hours.

5. The process for the preparation of a disubstituted diaryloxybenzoheterodiazole compound having general formula (I) according to claim 1, wherein:

in said step (d), said halogenated disubstituted diaryloxybenzoheterodiazole compound having general formula (VII) and said boronic compound having general formula (VIII) are used in molar ratios ranging from 1:2 to 1:4;

said step (d) is carried out in the presence of at least one catalyst containing palladium selected from the group consisting of [1,1'-bis (di-tert-butylphosphino) ferrocene]dichloropalladium (II) [Pd(dtbpf)Cl$_2$], palladium-tetrakistriphenylphosphine [Pd(PPh$_3$)$_4$], and bis-triphenylphosphine palladium dichloride [PdCl$_2$(PPh$_3$)$_2$]; said halogenated disubstituted diaryloxybenzoheterodiazole compound having general formula (VII) and said catalyst being used in molar ratios ranging from 100:1 to 100:3; and/or said step (d) is carried out in the presence of at least one organic base selected from the group consisting of trimethylamine, triethylamine, tri-iso-propylamine, diethyl-iso-propylamine, di-isopropylethylamine, 1,4-diazabicyclo[2.2.2]octane (DABCO), and mixtures thereof; said halogenated disubstituted diaryloxybenzoheterodiazole compound having general formula (VII) and said organic base being used in molar ratios ranging from 1:2 to 1:7; and/or in said step (d), said non-ionic surfactant is selected from non-ionic surfactants having an HLB greater than or equal to 10; and/or in said step (d), said hydrocarbon solvent is selected from aromatic hydrocarbons selected from the group consisting of toluene, xylene, iso-propylbenzene, or mixtures thereof; and aliphatic hydrocarbons selected from the group consisting of heptane, octane, decane, and mixtures thereof; and/or in said step (d) said mixture comprising water, at least one non-ionic surfactant, and at least one hydrocarbon solvent, comprises:

an aqueous solution comprising from 0.1% by weight to 20% by weight with respect to the total weight of said aqueous solution, of said at least one non-ionic surfactant;

at least one hydrocarbon solvent, volumetric ratio between said aqueous solution of said at least one non-ionic surfactant and said hydrocarbon solvent being ranging from 7:3 to 8:2;

said halogenated disubstituted diaryloxybenzoheterodiazole compound having general formula (VII) being used in said mixture in an amount as to have a molar concentration in said mixture ranging from 0.1 M to 1 M; and/or said step (d) is carried out at a temperature ranging from 25° C. to 90° C.; and/or said step (d) is carried out for a time ranging from 20 minutes to 70 minutes.

6. The process for the preparation of a disubstituted diaryloxybenzoheterodiazole compound having general formula (I) according to claim 1, wherein:

in said step (a), said halogenated benzoheterodiazole compound having general formula (II) and said 2-thienylboronic compound having general formula (III) are used in molar ratios ranging from 1:2 to 1:4 and/or said step (a) is carried out in the presence of at least one catalyst containing palladium selected from the group consisting of [1,1'-bis (di-tert-butylphosphino)ferrocene]dichloropalladium (II) [Pd(dtbpf)Cl$_2$], palladium-tetrakistriphenylphosphine [Pd(PPh$_3$)$_4$], and bis-triphenylphosphine palladium dichloride [PdCl$_2$(PPh$_3$)$_2$]; said halogenated benzoheterodiazole compound having general formula (II) and said catalyst being used in molar ratios ranging from 100:1 to 100:3; and/or said step (a) is carried out in the presence of at least one organic base selected from the group consisting of trimethylamine, triethylamine, tri-iso-propylamine, diethyl-iso-propylamine, di-isopropylethylamine, 1,4-diazabicyclo[2.2.2]octane (DABCO), and mixtures thereof; said halogenated benzoheterodiazole compound having general formula (II) and said organic base being used in molar ratios ranging from 1:2 to 1:7; and/or in said step (a), said non-ionic surfactant is selected from non-ionic surfactants having an HLB greater than or equal to 10; and/or in said step (a), said hydrocarbon solvent, optionally present, is selected from aromatic hydrocarbons from the group consisting of toluene, xylene, iso-propylbenzene, and mixtures thereof; and aliphatic hydrocarbons selected from the group consisting of heptane, octane, decane, or mixtures thereof; or mixtures thereof; and/or in said step (a) said mixture comprising water, at least one non-ionic surfactant and, optionally, at least one hydrocarbon solvent, comprises:

an aqueous solution comprising from 0.1% by weight to 20% by weight, with respect to the total weight of said aqueous solution, of said at least one non-ionic surfactant; and, optionally, at least one hydrocarbon solvent, volumetric ratio between said aqueous solution of said at least one non-ionic surfactant and said hydrocarbon solvent being ranging from 8:2 to 10:0;

said halogenated benzoheterodiazole compound having general formula (II) being used in said mixture in an amount as to have a molar concentration in said mixture ranging from 0.1 M to 1 M; and/or said step (a) is carried out at a temperature ranging from 25° C. to 80° C.; and/or said step (a) is carried out for a time ranging from 20 minutes to 60 minutes.

7. The process for the preparation of a disubstituted diaryloxybenzoheterodiazole compound having general formula (I) according to claim 2, wherein:

in said step (b), said halogenated disubstituted benzoheterodiazole compound having general formula (IV) and said aryl alcohol having general formula (V) are used in molar ratios ranging from 1:2 to 1:10; and/or said step (b) is carried out in the presence of at least one weak organic base selected from alkali metal carboxylates selected from the group consisting of potassium acetate, sodium acetate, cesium acetate, magnesium acetate, calcium acetate, potassium propionate, sodium propionate, cesium propionate, magnesium propionate, calcium propionate, and mixtures thereof; and alkali metal carbonates selected from the group consisting of lithium carbonate, potassium carbonate, sodium carbonate, cesium carbonate, magnesium carbonate, calcium carbonate, and mixtures thereof; said halogenated disubstituted benzoheterodiazole compound having general formula (IV) and said weak organic base being used in molar ratios ranging from 1:1 to 1:10; and/or said step (b) is carried out in the presence of at least one organic solvent selected from hydrocarbons selected from the group consisting of toluene, xylene, or mixtures thereof; and dipolar aprotic solvents selected from the group consisting of N,N-dimethylformamide, N-methylpyrrolidone, dimethyl sulfoxide, or mixtures thereof; and mixtures thereof; said halogenated disubstituted benzoheterodiazole compound having general formula (IV) being used in said organic solvent in an amount as to have a molar concentration in said organic solvent ranging from 0.05 M to 2 M; and/or said step (b) is carried out in the presence of at least one crown ether selected from the group consisting of 18-crown-6, dibenzo-18-crown-6, dicyclohexyl-18-crown-6, dibenzo-24-crown-8, 12-crown-4, 15-crown-5, cyclohexyl-12-crown-4, tribenzo-18-crown-6, tetrabenzo-18-crown-6, dibenzo-26-crown-6, and mixtures thereof; said crown ether being used in an amount ranging from 1 mol % to 10 mol % with respect to the moles of said weak organic base; and/or said step (b) is carried out at a temperature ranging from 60° C. to 95° C.; and/or said step (b) is carried out for a time ranging from 1 hour to 24 hours.

8. The process for the preparation of a disubstituted diaryloxybenzoheterodiazole compound having general formula (I) according to claim 3, wherein:

in said step (c), said disubstituted diaryloxybenzoheterodiazole compound having general formula (VI) and said N-haloimide are used in molar ratios ranging from 1:2 to 1:3; and/or said step (c) is carried out in the presence of at least one organic solvent selected from the group consisting of 1,2-dimethoxyethane, 1,4-dioxane, tetrahydrofuran, 2-methyl-tetrahydrofuran, or mixtures thereof; said disubstituted diaryloxybenzoheterodiazole compound having general formula (VI) being used in said organic solvent in an amount as to have a molar concentration in said organic solvent ranging from 0.01 M to 5 M; and/or said step (c) is carried out at a temperature ranging from 20° C. to 50° C.; and/or said step (c) is carried out for a time ranging from 1 hour to 24 hours.

9. The process for the preparation of a disubstituted diaryloxybenzoheterodiazole compound having general formula (I) according to claim 2, wherein:

in said step (c), said disubstituted diaryloxybenzoheterodiazole compound having general formula (VI) and said N-haloimide are used in molar ratios ranging from 1:2 to 1:3; and/or said step (c) is carried out in the presence of at least one organic solvent selected from the group consisting of 1,2-dimethoxyethane, 1,4-dioxane, tetrahydrofuran, 2-methyl-tetrahydrofuran, or mixtures thereof; said disubstituted diaryloxybenzoheterodiazole compound having general formula (VI) being used in said organic solvent in an amount as to have a molar concentration in said organic solvent ranging from 0.01 M to 5 M; and/or said step (c) is carried out at a temperature ranging from 20° C. to 50° C.; and/or said step (c) is carried out for a time ranging from 1 hour to 24 hours.

10. The process for the preparation of a disubstituted diaryloxybenzoheterodiazole compound having general formula (I) according to claim 3, wherein:

in said step (c), said disubstituted diaryloxybenzoheterodiazole compound having general formula (VI) and said N-haloimide are used in molar ratios ranging from 1:2 to 1:3; and/or said step (c) is carried out in the presence of at least one organic solvent selected from the group consisting of 1,2-dimethoxyethane, 1,4-dioxane, tetrahydrofuran, 2-methyl-tetrahydrofuran, or mixtures thereof; said disubstituted diaryloxybenzoheterodiazole compound having general formula (VI) being used in said organic solvent in an amount as to have a molar concentration in said organic solvent ranging from 0.01 M to 5 M; and/or said step (c) is carried out at a temperature ranging from 20° C. to 50° C.; and/or said step (c) is carried out for a time ranging from 1 hour to 24 hours.

11. The process for the preparation of a disubstituted diaryloxybenzoheterodiazole compound having general formula (I) according to claim 2, wherein:

in said step (d), said halogenated disubstituted diaryloxybenzoheterodiazole compound having general formula (VII) and said boronic compound having general formula (VIII) are used in molar ratios ranging from 1:2 to 1:4;

said step (d) is carried out in the presence of at least one catalyst containing palladium selected from the group consisting of [1,1'-bis (di-tert-butylphosphino) ferrocene]dichloropalladium (II) [Pd(dtbpf)Cl$_2$], palladium-tetrakistriphenylphosphine [Pd(PPh$_3$)$_4$], and bis-triphenylphosphine palladium dichloride [PdCl$_2$(PPh$_3$)$_2$]; said halogenated disubstituted diaryloxybenzoheterodiazole compound having general formula (VII) and said catalyst being used in molar ratios ranging from 100:1 to 100:3; and/or said step (d) is carried out in the presence of at least one organic base selected from the group consisting of trimethylamine, triethylamine, tri-iso-propylamine, diethyl-iso-propylamine, di-isopropylethylamine, 1,4-diazabicyclo[2.2.2]octane (DABCO), and mixtures thereof; said halogenated disubstituted diaryloxybenzoheterodiazole compound having general formula (VII) and said organic base being used in molar ratios ranging from 1:2 to 1:7; and/or in said step (d), said non-ionic surfactant is selected from non-ionic surfactants having an HLB greater than or equal to 10; and/or in said step (d), said hydrocarbon solvent is selected from aromatic hydrocarbons selected from the group consisting of toluene, xylene, iso-propylbenzene, or mixtures thereof; and aliphatic hydrocarbons selected from the group consisting of heptane, octane, decane, and mixtures thereof; and/or in said step (d) said mixture comprising water, at least one non-ionic surfactant, and at least one hydrocarbon solvent, comprises:

an aqueous solution comprising from 0.1% by weight to 20% by weight, with respect to the total weight of said aqueous solution, of said at least one non-ionic surfactant;

at least one hydrocarbon solvent, volumetric ratio between said aqueous solution of said at least one non-ionic surfactant and said hydrocarbon solvent being ranging from 7:3 to 8:2;

said halogenated disubstituted diaryloxybenzoheterodiazole compound having general formula (VII) being used in said mixture in an amount as to have a molar concentration in said mixture ranging from 0.1 M to 1 M; and/or said step (d) is carried out at a temperature ranging from 25° C. to 90° C.; and/or said step (d) is carried out for a time ranging from 20 minutes to 70 minutes.

12. The process for the preparation of a disubstituted diaryloxybenzoheterodiazole compound having general formula (I) according to claim 3, wherein:

in said step (d), said halogenated disubstituted diaryloxybenzoheterodiazole compound having general formula (VII) and said boronic compound having general formula (VIII) are used in molar ratios ranging from 1:2 to 1:4;

said step (d) is carried out in the presence of at least one catalyst containing palladium selected from the group consisting of [1,1'-bis (di-tert-butylphosphino) ferrocene]dichloropalladium (II) [Pd(dtbpf)Cl$_2$], palladium-tetrakistriphenylphosphine [Pd(PPh$_3$)$_4$], and bis-triphenylphosphine palladium dichloride [PdCl$_2$(PPh$_3$)$_2$]; said halogenated disubstituted diaryloxybenzoheterodiazole compound having general formula (VII) and said catalyst being used in molar ratios ranging from 100:1 to 100:3; and/or said step (d) is carried out in the presence of at least one organic base selected from the group consisting of trimethylamine, triethylamine, tri-iso-propylamine, diethyl-iso-propylamine, di-isopropylethylamine, 1,4-diazabicyclo[2.2.2]octane (DABCO), and mixtures thereof; said halogenated disubstituted diaryloxybenzoheterodiazole compound having general formula (VII) and said organic base being used in molar ratios ranging from 1:2 to 1:7; and/or in said step (d), said non-ionic surfactant is selected from non-ionic surfactants having an HLB greater than or equal to 10; and/or in said step (d), said hydrocarbon solvent is selected from aromatic hydrocarbons selected from the group consisting of toluene, xylene, iso-propylbenzene, or mixtures thereof; and aliphatic hydrocarbons selected from the group consisting of heptane, octane, decane, and mixtures thereof; and/or in said step (d) said mixture comprising water, at least one non-ionic surfactant, and at least one hydrocarbon solvent, comprises:

an aqueous solution comprising from 0.1% by weight to 20% by weight, with respect to the total weight of said aqueous solution, of said at least one non-ionic surfactant;

at least one hydrocarbon solvent, volumetric ratio between said aqueous solution of said at least one non-ionic surfactant and said hydrocarbon solvent being ranging from 7:3 to 8:2;

said halogenated disubstituted diaryloxybenzoheterodiazole compound having general formula (VII) being used in said mixture in an amount as to have a molar concentration in said mixture ranging from 0.1 M to 1 M; and/or said step (d) is carried out at a temperature ranging from 25° C. to 90° C.; and/or said step (d) is carried out for a time ranging from 20 minutes to 70.

13. The process for the preparation of a disubstituted diaryloxybenzoheterodiazole compound having general formula (I) according to claim 4, wherein:

in said step (d), said halogenated disubstituted diaryloxybenzoheterodiazole compound having general formula (VII) and said boronic compound having general formula (VIII) are used in molar ratios ranging from 1:2 to 1:4;

said step (d) is carried out in the presence of at least one catalyst containing palladium selected from the group consisting of [1,1'-bis (di-tert-butylphosphino) ferrocene]dichloropalladium (II) [Pd(dtbpf)Cl$_2$], palladium-tetrakistriphenylphosphine [Pd(PPh$_3$)$_4$], and bis-triphenylphosphine palladium dichloride [PdCl$_2$(PPh$_3$)$_2$]; said halogenated disubstituted diaryloxybenzoheterodiazole compound having general formula (VII) and said catalyst being used in molar ratios ranging from 100:1 to 100:3; and/or said step (d) is carried out in the presence of at least one organic base selected from the group consisting of trimethylamine, triethylamine, tri-iso-propylamine, diethyl-iso-propylamine, di-isopropylethylamine, 1,4-diazabicyclo[2.2.2]octane (DABCO), and mixtures thereof; said halogenated disubstituted diaryloxybenzoheterodiazole compound having general formula (VII) and said organic base being used in molar ratios ranging from 1:2 to 1:7; and/or in said step (d), said non-ionic surfactant is selected from non-ionic surfactants having an HLB greater than or equal to 10; and/or in said step (d), said hydrocarbon solvent is selected from aromatic hydrocarbons selected from the group consisting of toluene, xylene, iso-propylbenzene, or mixtures thereof; and aliphatic hydrocarbons selected from the group consisting of heptane, octane, decane, and mixtures thereof; and/or in said step (d) said mixture comprising water, at least one non-ionic surfactant, and at least one hydrocarbon solvent, comprises:

an aqueous solution comprising from 0.1% by weight to 20% by weight, with respect to the total weight of said aqueous solution, of said at least one non-ionic surfactant;

at least one hydrocarbon solvent, volumetric ratio between said aqueous solution of said at least one non-ionic surfactant and said hydrocarbon solvent being ranging from 7:3 to 8:2;

said halogenated disubstituted diaryloxybenzoheterodiazole compound having general formula (VII) being used in said mixture in an amount as to have a molar concentration in said mixture ranging from 0.1 M to 1 M; and/or said step (d) is carried out at a temperature ranging from 25° C. to 90° C.; and/or said step (d) is carried out for a time ranging from 20 minutes to 70 minutes.

* * * * *